United States Patent [19]

Chen

[11] Patent Number: 5,328,370
[45] Date of Patent: Jul. 12, 1994

[54] DENTAL TOOL ASSEMBLY

[76] Inventor: Shih-Chieh Chen, No. 3, Lane 68, Liou Yang East Street, Taichung, Taiwan

[21] Appl. No.: 115,311

[22] Filed: Sep. 1, 1993

[51] Int. Cl.⁵ .............................. A61C 3/00
[52] U.S. Cl. ...................... 433/147; 433/146; 403/348
[58] Field of Search .............. 433/141, 146, 147, 127, 433/128, 30; 403/300, 348

[56] References Cited

U.S. PATENT DOCUMENTS

| | | | |
|---|---|---|---|
| 2,379,984 | 7/1945 | Nereaux | 403/348 X |
| 3,611,411 | 5/1972 | FLick | 403/348 |
| 4,393,539 | 7/1983 | Weissman | 433/147 X |
| 4,400,158 | 8/1983 | Garcia | 433/127 |
| 4,661,062 | 4/1987 | Seigneurin | 433/128 |
| 5,028,181 | 7/1991 | Jenkins et al. | 433/128 X |

Primary Examiner—Robert P. Swiatek
Assistant Examiner—Nicholas D. Lucchesi
Attorney, Agent, or Firm—Charles E. Baxley

[57] ABSTRACT

A dental tool device includes a rod, a pair of stops disposed in the rod, two protrusions formed on each of the stops, a tool having a stub engaged in the rod, and a block fixed to the stub of the tool, two cusps formed on the block, the cusps of the block are engaged between the protrusions of the stops when the block passes the stops and is rotated relative to the stops, the tool is disposable when it is disengaged from the rod.

1 Claim, 2 Drawing Sheets

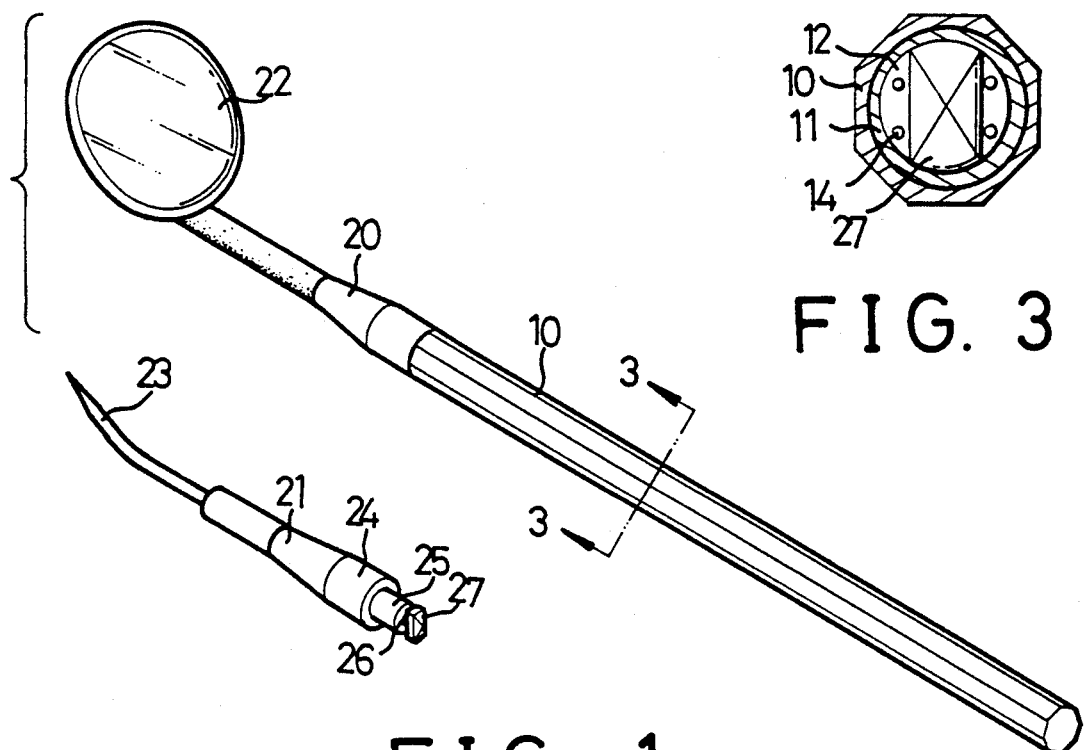
FIG. 3
FIG. 1
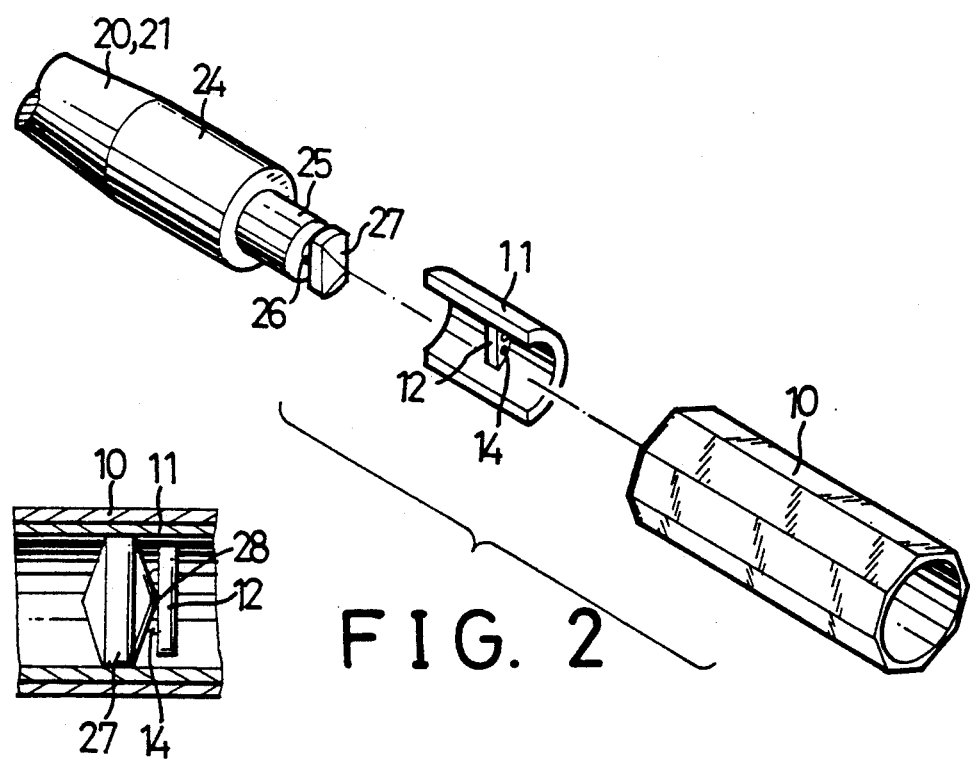
FIG. 2
FIG. 4

DENTAL TOOL ASSEMBLY

BACKGROUND OF THE INVENTION

1. Field of the Invention

The present invention relates to a tool, and more particularly to a dental tool assembly.

2. Description of the Prior Art

Typical dental tools, as shown in FIG. 5, comprise at least two tools 90, 92 having a pin element 91 and a mirror 93 provided on one end thereof respectively, the pin element 91 and the mirror 93 are each solidly fixed on a rod and can not be disengaged from the rod such that the pin element 91 and the mirror 93 can not be changed.

The present invention has arisen to mitigate and/or obviate the afore-described disadvantages of the conventional dental tools.

SUMMARY OF THE INVENTION

The primary objective of the present invention is to provide a dental tool assembly including one or more tools which can be changed easily.

In accordance with one aspect of the invention, there is provided a dental tool assembly comprising a rod including an open end, a first engaging means provided in the open end of the rod, and at least one tool including a stub engaged in the open end of the rod, and a second engaging means provided on the stub of the tool and engagable with the first engaging means. The first engaging means includes a pair of stops oppositely provided in the open end of the rod, a third engaging means provided on each of the stops, the second engaging means includes an extension extended from the stub and a block fixed to the extension, the block includes a fourth engaging means provided thereon, the fourth engaging means is engaged with the third engaging means when the block is engaged through the stops and is rotated relative to the stops. The third engaging means includes two protrusions formed on each of the stops, and the fourth engaging means includes two cusps formed on the block and facing toward the stub, the cusps are engaged between the protrusions when the block is rotated relative to the stops.

Further objectives and advantages of the present invention will become apparent from a careful reading of the detailed description provided hereinbelow, with appropriate reference to the accompanying drawings.

BRIEF DESCRIPTION OF THE DRAWINGS

FIG. 1 is a perspective view of a dental tool assembly in accordance with the present invention, in which one of the tools is shown in an exploded way;

FIG. 2 is an enlarged partial exploded view of the dental tool assembly;

FIG. 3 is a cross sectional view taken along lines 3—3 of FIG. 1;

FIG. 4 is a schematic view illustrating the engagement of the tool and the rod.

DETAILED DESCRIPTION OF THE PREFERRED EMBODIMENT

Figure 5:
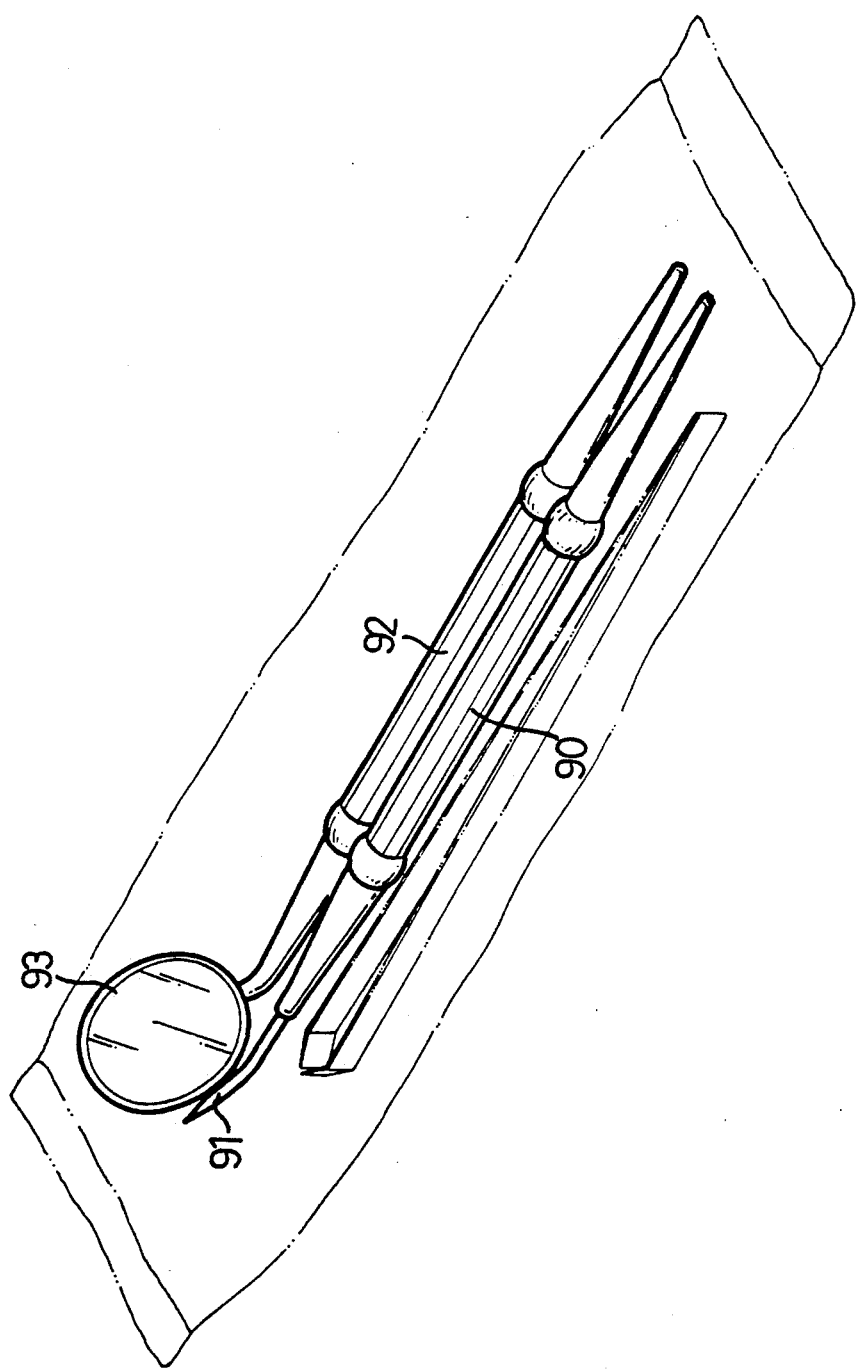
FIG. 5 is a schematic view illustrating the conventional dental tool assembly.

Referring to the drawings, and initially to FIGS. 1 and 2, a dental tool assembly in accordance with the present invention comprises a rod 10 having one or more tools 20, 21 engaged thereto, the tools 20, 21 can be easily disengaged from the rod 10 and can be easily changed, in addition, the rod 10 can still be used and the tools 20, 21 are disposable after using.

The rod 10 includes an open end having a sleeve 11 fixed therein, a pair of stops 12 oppositely fixed in the sleeve 11 and each having two protrusions 14 formed thereon. The tool 20 includes a mirror 22 provided on one end thereof, the other tool 21 includes a pin element 23 provided on one end thereof, the other end 24 of the tools 20, 21 have an outer diameter equal to that of the rod 10, a stub 25 extended from the other end 24 of each of the tools 20, 21, the stub 25 having an outer diameter equal to the inner diameter of the sleeve 11 such that the stub 25 can be engaged in the sleeve 11, an extension 26 extended from the stub 25 and having a block 27 fixed thereto.

As best shown in FIG. 3, the space formed between the two stops 12 is preferably equal to the size of the block 27 such that the block 27 can be engaged through the space formed between the two stops 12, or the block 27 and the stops 12 form a circular outer peripheral surface as shown in FIG. 3, the block 27 includes two cusps 28 (FIG. 4) formed thereon and facing toward the stub 25, when the block 27 is engaged through the space between the stops 12 and when the tool 20 is rotated for 90 degrees, the cusps 28 of the block 27 may move over one of the protrusions 14 of the respective stops 12 and may be engaged between the protrusions 14, best shown in FIG. 4, such that the tools 20, 21 can be engaged to the rod 10. After using, the tools 20, 21 are disposable after disengaging from the rod 10, and the rod 10 can still be used.

Accordingly, the dental tool assembly in accordance with the present invention includes one or more tools which can be easily engaged to a rod and can be disengaged from the rod such that the tools are disposable after using.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A dental tool assembly comprising a rod including an open end, a first engaging means provided in said open end, at least one tool including a stub engageable in said open end, a second engaging means provided on said stub of said at least one tool and engageable with said first engaging means, whereby said at least one tool is disposable when said at least one tool is disengaged from said rod, said first engaging means including a pair of stops oppositely provided in said open end, a third engaging means provided on each of said stops, said second engaging means including an extension extended from said stub and a block fixed to said extension, said block including a fourth engaging means provided thereon, said fourth engaging means engageable with said third engaging means when said block is engaged inward of said stops and is rotated relative to said stops, said third engaging means including two protrusions, said fourth engaging means including two cusps formed on said block and facing toward said stub, said cusps engageable between said protrusions when said block is rotated relative to said stops.

* * * * *